(12) United States Patent
Pigamo et al.

(10) Patent No.: US 10,011,544 B2
(45) Date of Patent: *Jul. 3, 2018

(54) CATALYTIC GAS PHASE FLUORINATION

(71) Applicant: Arkema France, Colombes (FR)

(72) Inventors: Anne Pigamo, Francheville (FR); Nicolas Doucet, Lyons (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/453,986

(22) Filed: Mar. 9, 2017

(65) Prior Publication Data
US 2017/0174587 A1 Jun. 22, 2017

Related U.S. Application Data

(63) Continuation of application No. 15/096,603, filed on Apr. 12, 2016, now Pat. No. 9,624,146, which is a continuation of application No. 13/980,665, filed as application No. PCT/IB2011/000314 on Jan. 21, 2011, now Pat. No. 9,340,473.

(51) Int. Cl.
*C07C 17/25* (2006.01)
*C07C 17/20* (2006.01)
*B01J 23/86* (2006.01)
*B01J 27/125* (2006.01)
*B01J 38/12* (2006.01)

(52) U.S. Cl.
CPC .......... *C07C 17/206* (2013.01); *B01J 23/866* (2013.01); *B01J 27/125* (2013.01); *B01J 38/12* (2013.01)

(58) Field of Classification Search
CPC .............................. C07C 17/25; C07C 17/206
See application file for complete search history.

(56) References Cited

U.S. PATENT DOCUMENTS

| | | |
|---|---|---|
| 3,341,281 A | 9/1967 | Davis et al. |
| 3,431,067 A | 3/1969 | Kato et al. |
| 4,902,838 A | 2/1990 | Manzer et al. |
| 5,281,568 A | 1/1994 | Scott et al. |
| 5,731,481 A | 3/1998 | Cheminal et al. |
| 5,739,070 A | 4/1998 | Ebmeyer et al. |
| 6,649,560 B2 | 11/2003 | Lacroix et al. |
| 7,435,700 B2 | 10/2008 | Amos |
| 7,485,598 B2 | 2/2009 | Elsheikh et al. |
| 2009/0240090 A1 | 9/2009 | Merkel et al. |
| 2010/0331583 A1 | 12/2010 | Johnson et al. |
| 2012/0059202 A1 | 3/2012 | Elsheikh et al. |

FOREIGN PATENT DOCUMENTS

| | | |
|---|---|---|
| CN | 1071348 | 4/1993 |
| EP | 0 475 693 A1 | 3/1992 |
| EP | 0 939 071 | 1/1999 |
| WO | WO 2004/018095 | 3/2004 |
| WO | WO 2007/079431 | 12/2007 |
| WO | WO 2008/002500 | 3/2008 |
| WO | WO 2008/054781 | 8/2008 |
| WO | WO 2008/040969 | 10/2008 |
| WO | WO 2009/003084 | 12/2008 |
| WO | WO 2009/015317 | 1/2009 |
| WO | WO 2009/118628 | 10/2009 |
| WO | WO 2010/123154 | 10/2010 |

OTHER PUBLICATIONS

International Search Report for PCT/IB2011/000314 dated Oct. 14, 2011.

*Primary Examiner* — Medhanit W Bahta
(74) *Attorney, Agent, or Firm* — NK Patent Law, PLLC

(57) ABSTRACT

The present invention relates to a fluorination process, comprising:
  an activation stage comprising contacting a fluorination catalyst with an oxidizing agent-containing gas flow for at least one hour; and
  at least one reaction stage comprising reacting a chlorinated compound with hydrogen fluoride in gas phase in the presence of the fluorination catalyst, so as to produce a fluorinated compound.

19 Claims, No Drawings

CATALYTIC GAS PHASE FLUORINATION

CROSS-REFERENCE TO RELATED APPLICATIONS

This application is a Continuation of U.S. patent application Ser. No. 15/096,603, filed Apr. 12, 2016, now allowed; which is a Continuation of U.S. patent application Ser. No. 13/980,665 filed Oct. 8, 2013, issued as U.S. Pat. No. 9,340,473; which is a National Stage application of International Application No. PCT/IB2011/000314 filed Jan. 21, 2011, each of which is incorporated by reference herein.

FIELD OF THE INVENTION

The present invention relates to the gas phase catalyzed fluorination of a chlorinated compound to a fluorinated compound using hydrogen fluoride (HF), and notably the gas phase catalyzed fluorination of 2-chloro-3,3,3-trifluoro-1-propene (HFCO-1233xf) or of 1,1,1,2,3-pentachloropropane to produce 2,2,2,3-tetrafluoropropene (HFO-1234yf).

The products obtained owing to the invention, such as HFO-1234yf, are known to have utility as a foam blowing agent, refrigerant, aerosol propellant, heat transfer media, fire extinguisher, etc. HFO-1234yf is also known to have zero Ozone Depletion Potential (ODP) and a very low Global Warming Potential (GWP) of much less than 150.

BACKGROUND OF THE INVENTION

The Montreal Protocol for the protection of the ozone layer mandated the phase out of the use of chlorofluorocarbons (CFCs). Materials friendlier to the ozone layer, such as hydrofluorocarbons (HFCs), e.g. HFC-134a, replaced chlorofluorocarbons. The latter compounds have proven to be greenhouse gases, causing global warming. They were regulated by the Kyoto Protocol on Climate Change. With the continued concern over global climate change there is an increasing need to develop technologies to replace those with high ozone depletion potential (ODP) and high global warming potential (GWP). Though hydrofluorocarbons (HFCs), being non-ozone depleting compounds, have been identified as alternatives to chlorofluorocarbons (CFCs) and hydrochlorofluorocarbons (HCFCs) as solvents, cleaning agents and heat transfer fluids, they still tend to have significant GWP. Hydrofluoroolefins (HFO) have been identified as potential alternatives with zero ODP and low GWP.

Hence, numerous documents teach processes for making such HFOs, including HFO-1234yf.

For example, WO 2007/079431 discloses processes for the production of fluorinated olefins, including hydrofluoropropenes. The processes which are broadly described as a single reaction or two or more reactions involve fluorination of a compound of the formula $C(X)_mCCl(Y)_nC(X)_m$ to at least one compound of formula $CF_3CF=CHZ$, where each X, Y and Z is independently H, F, Cl, I or Br and each m is independently 1, 2 or 3 and n is 0 or 1. HFO-1234yf is prepared by fluorinating HFCO-1233xf into 1,1,1,2-tetrafluoro-2-chloropropane (HCFC-244bb), followed by dehydrochlorination. HFCO-1233xf is prepared by fluorination of the corresponding chlorinated precursor ($CCl_2=CClCH_2Cl$).

EP-A-939071 discloses, among many possibilities, gas-phase fluorination of a halogenated propene (according to a very long list) into a fluorinated propene (including in the list HFO-1234yf).

WO 2008/054781 discloses a variety of processes for producing a variety of fluoropropanes and halofluoropropenes by reacting halopropanes or halopropenes with HF, optionally in the presence of a catalyst. It discloses a process for making HFO-1234yf by reacting 2,3-dichloro-1,1,1-trifluoropropane (HCFC-243db) in the presence of HF, on a catalyst, especially Cr/Co (98/2). Reaction products comprise HFO-1234yf and HFCO-1233xf, the latter being the main product; other products are 1-chloro-3,3,3-trifluoro-1-propene (HFCO-1233zd) as well as 1,1,1,2,2-pentafluoropropane (HFC-245cb) and 1,3,3,3-tetrafluoro-1-propene (HFO-1234ze).

WO 2008/002500 discloses a process for making a mixture of HFO-1234yf and HFO-1234ze by catalytic conversion of 1,1,1,2,3-pentafluoropropane (HFC-245eb) on a dehydrofluorination catalyst.

WO 2008/040969 discloses a process comprising dehydrochlorination of HCFC-243db into HFCO-1233 (xf as well as zd), followed by a reaction involving formation of 1,1,1,2-tetrafluoro-2-chloropropane (HCFC-244bb) and later formation of the desired HFO-1234yf through dehydrochlorination. Example 1 of said document discloses a gas phase reaction at atmospheric pressure of HCFC-243db with HF on a Zn/chromia catalyst, whereby HFO-1234yf and HFCO-1233xf are formed, together with a small amount of HFC-245cb.

WO 2009/015317 discloses the reaction of a chlorinated compound which can be 1,1,2,3-tetrachloro-1-propene (HCO-1230xa), 1,1,1,2,3-pentachloropropane (HCC-240db) or 2,3,3,3-tetrachloro-1-propene (HCO-1230xf) with HF, in gas phase, on a catalyst and in the presence of at least one stabilizer. This process makes it possible to obtain 2-chloro-3,3,3-trifluoro-1-propene (HFCO-1233xf).

US 2009/0240090 discloses a process for making 2,3,3,3-tetrafluoro-1-propene (HFO-1234yf) starting from a compound of formula (I) $CX_2=CClCH_2X$, or formula (II) $CX_3CCl=CH_2$ or formula (III) $CX_3CHClCH_2X$ with X=F, Cl, Br, I. The process comprises three steps, which can be followed by purification. The process includes recycling steps allowing higher conversions and yields.

WO 2010/123154 is directed to a process for producing HFO-1234yf starting from HFCO-1233xf, by reacting it with HF in the presence of oxygen and a catalyst comprising chromium oxide or fluorinated chromium oxide.

However, there is still a need to provide an improved process for making fluoroolefins such as HFO-1234yf, having in particular an improved conversion rate and/or an improved selectivity and/or which is effective over a longer period of time.

SUMMARY OF THE INVENTION

The present invention provides a fluorination process, comprising:
  an activation stage comprising contacting a fluorination catalyst with an oxidizing agent-containing gas flow for at least one hour; and
  at least one reaction stage comprising reacting a chlorinated compound with hydrogen fluoride in gas phase in the presence of the fluorination catalyst, so as to produce a fluorinated compound.

According to one embodiment, the process comprises a plurality of reaction stages alternating with a plurality of regeneration stages, wherein the reaction stages comprise reacting the chlorinated compound with hydrogen fluoride in gas phase in the presence of the fluorination catalyst, and the regeneration stages comprise contacting the fluorination catalyst with an oxidizing agent-containing gas flow.

According to one embodiment, the oxidizing agent-containing gas flow of the activation stage and/or the regeneration stages is an oxygen-containing gas flow.

According to one embodiment, the activation stage and/or the regeneration stages comprise contacting the fluorination catalyst with the oxidizing agent-containing gas flow for at least 2 hours, preferably for at least 4 hours, more preferably for at least 10 hours, and even more preferably for at least 15 hours.

According to one embodiment, the oxidizing agent-containing gas flow of the activation stage and/or the regeneration stages contains hydrogen fluoride in addition to the oxidizing agent, and the proportion of oxidizing agent in the oxidizing agent-containing gas flow of the activation stage and/or the regeneration stages is preferably from 2 to 98 mol %, and more preferably from 5 to 50 mol %, relative to the total amount oxidizing agent and hydrogen fluoride.

According to one embodiment, the oxidizing agent-containing gas flow of the activation stage and/or the regeneration stages does not contain hydrogen fluoride, and preferably is air.

According to one embodiment, the activation stage and/or the regeneration stages comprise contacting the fluorination catalyst with a hydrogen fluoride gas flow, either:
  before contacting the fluorination catalyst with the oxidizing agent-containing gas flow; or
  after contacting the fluorination catalyst with the oxidizing agent-containing gas flow.

According to one embodiment, the activation stage comprises a preliminary step of reacting the chlorinated compound with hydrogen fluoride in gas phase in the presence of the fluorination catalyst, prior to contacting the chlorinated compound with the oxidizing agent-containing gas flow.

According to one embodiment, the oxidizing agent-containing gas flow is contacted with the fluorination catalyst during the activation stage and/or the regeneration stages at a temperature of from 250 to 500° C., preferably from 300 to 400° C., more preferably from 350 to 380° C.

According to one embodiment, the fluorinated compound is a fluoroolefin, preferably a fluoropropene, and more preferably 2,3,3,3-tetrafluoro-1-propene.

According to one embodiment, the chlorinated compound is selected from hydrochlorocarbons, hydrochlorofluorocarbons and hydrochlorofluoroolefins, and is preferably selected from 2-chloro-3,3,3-trifluoro-1-propene, 1,1,1,2,3-pentachloropropane, 1,1,2,2,3-pentachloropropane, 2,3-dichloro-1,1,1-trifluoropropane, 2,3,3,3-tetrachloro-1-propene and 1,1,2,3 tetrachloro-1-propene, and is more preferably 2-chloro-3,3,3-trifluoro-1-propene.

According to one embodiment, the fluorination catalyst is a supported catalyst, and is preferably supported on a support selected from fluorinated alumina, fluorinated chromia, fluorinated activated carbon or graphite carbon.

According to one embodiment, the fluorination catalyst is an unsupported catalyst.

According to one embodiment, the fluorination catalyst further comprises a co-catalyst selected from Co, Zn, Mn, Mg, V, Mo, Te, Nb, Sb, Ta, P, Ni or mixtures thereof, preferably Ni, and said co-catalyst is preferably present in an amount from about 1-10 wt % of said fluorination catalyst.

According to one embodiment, the fluorination catalyst is a mixed chromium/nickel catalyst, the atomic ratio of nickel to chromium being preferably from 0.5 to 2 and more preferably approximately 1.

According to one embodiment, the molar ratio of hydrogen fluoride to 2-chloro-3,3,3-trifluoro-1-propene is from 3:1 to 150:1, preferably 4:1 to 70:1, more preferably 5:1 to 50:1, and even more preferably from 10:1 to 30:1.

According to one embodiment, the reaction stages are carried out at a pressure of from 1 to 20 bars, preferably from 5 to 15 bars, more preferably from 7 to 10 bars.

According to one embodiment, the reaction stages are carried out at a temperature of from 200 to 450° C., preferably from 300 to 430° C., more preferably from 320 to 420° C. and even more preferably from 340 to 380° C.

According to one embodiment, the contact time between hydrogen fluoride and the chlorinated compound during the reaction stages is from 6 to 100 s, preferably from 10 to 80 s, more preferably from 15 to 50 s.

According to one embodiment, the reaction stages are carried out in the presence of an oxidizing agent such as oxygen, the ratio of oxygen being preferably from 0.05 to 15 mole %, more preferably from 0.5 to 10 mole %, and most preferably from 5 to 10 mole %, with respect to the total amount of chlorinated compound and oxygen.

The present invention fulfils the need expressed in the prior art. In particular, it provides an improved process for making fluoroolefins such as HFO-1234yf.

For instance, the conversion rate of HFCO-1233xf is improved relative to the teaching of WO 2010/123154.

The above results are made possible owing to the surprising finding made by the present inventors that the performances of the reaction are increased when the fluorination catalyst is activated in the presence of an oxidizing agent such as oxygen.

DETAILED DESCRIPTION OF EMBODIMENTS OF THE INVENTION

The invention will now be described in more detail without limitation in the following description.

As used herein, percentages are by molar percent unless specified otherwise.

Fluorination Reaction

In the fluorination reaction of the invention, a chlorinated compound is converted to a fluorinated compound through a reaction with hydrogen fluoride (HF) in the presence of a catalyst.

The "chlorinated compound" can be any molecule having a chlorine atom, and the "fluorinated compound" can be any molecule having a fluorine atom.

Preferably, the chlorinated compound is a C2 or C3 or C4 or C5 alkane or alkene compound, which is linear or branched (preferably linear), having one or more substituents selected from F, Cl, I and Br (preferably from F and Cl), at least one of the substituents being Cl.

Preferably, the fluorinated compound is a C2 or C3 or C4 or C5 alkane or alkene compound (preferably alkene), which is linear or branched (preferably linear), having one or more substituents selected from F, Cl, I and Br (preferably from F and Cl), at least one of the substituents being F.

More preferably, the chlorinated compound is a C3 alkane or alkene compound having one or more substituents selected from F, Cl, I and Br (preferably F and Cl), at least one of the substituents being Cl; and the fluorinated compound is a C3 alkene compound having one or more substituents selected from F, Cl, I and Br (preferably F and Cl), at least one of the substituents being F.

Alternatively, the chlorinated compound can be a C4 alkane or alkene compound having one or more substituents selected from F, Cl, I and Br (preferably F and Cl), at least one of the substituents being Cl; and the fluorinated compound is a C4 alkene compound having one or more substituents selected from F, Cl, I and Br (preferably F and Cl), at least one of the substituents being F.

According to one embodiment, the fluorinated compound is a hydrofluoroolefin (and thus has no chlorine substituent).

Preferably, during the reaction, at least one Cl substituent in the chlorinated compound is replaced by an F substituent.

The conversion of the chlorinated compound to the fluorinated compound comprises direct conversion (i.e. in a single reaction step or under essentially one set of reaction conditions) and indirect conversion (i.e. through two or more reaction steps or using more than one single set of reaction conditions).

Most preferred fluorination reactions are the following:
- 2-chloro-3,3,3-trifluoro-1-propene (HFCO-1233xf) to 2,3,3,3-tetrafluoro-1-propene (HFO-1234yf);
- 1,1,1,2,3-pentachloropropane (HCC-240db) to 2,3,3,3-tetrafluoro-1-propene (HFO-1234yf);
- 1,1,2,2,3-pentachloropropane (HCC-240aa) to 2,3,3,3-tetrafluoro-1-propene (HFO-1234yf);
- 2,3-dichloro-1,1,1-trifluoropropane (HCFC-243db) to 2,3,3,3-tetrafluoro-1-propene (HFO-1234yf);
- 1,1,2,3 tetrachloro-1-propene (HCO-1230xa) to 2,3,3,3-tetrafluoro-1-propene (HFO-1234yf);
- 2,3,3,3 tetrachloro-1-propene (HCO-1230xf) to 2,3,3,3-tetrafluoro-1-propene (HFO-1234yf);
- 1,1,1,2,3-pentachloropropane (HCC-240db) to 2-chloro-3,3,3-trifluoro-1-propene (HFCO-1233xf);
- 1,1,2,2,3-pentachloropropane (HCC-240aa) to 2-chloro-3,3,3-trifluoro-1-propene (HFCO-1233xf);
- 2,3-dichloro-1,1,1-trifluoropropane (HCFC-243db) to 2-chloro-3,3,3-trifluoro-1-propene (HFCO-1233xf);
- 1,1,2,3 tetrachloro-1-propene (HCO-1230xa) to 2-chloro-3,3,3-trifluoro-1-propene (HFCO-1233xf);
- 2,3,3,3 tetrachloro-1-propene (HCO-1230xf) to 2-chloro-3,3,3-trifluoro-1-propene (HFCO-1233xf).

The fluorination reaction can be carried out with an HF molar ratio typically from 3:1 to 150:1, at a contact time from 6 to 100 s and a pressure from atmospheric pressure to 20 bars. The catalyst bed temperature can be from 200 to 450° C.

In order to prevent a fast deactivation of the catalyst during the fluorination reaction, an oxidizing agent (such as oxygen or chlorine) can be added, for example at a rate of from 0.05 to 15 mol %, with respect to the mixture of oxidizing agent plus chlorinated compound.

Catalyst

The fluorination catalyst used in the present invention can be supported or unsupported.

It can be for example a catalyst based on a metal including a transition metal oxide or a derivative or halide or oxyhalide such a metal. Catalysts are e.g. $FeCl_3$, chromium oxyfluoride, chromium oxides (that can optionally be subject to fluorination treatments), chromium fluorides, and mixtures thereof.

Other possible catalysts are the catalysts supported on carbon catalysts based on antimony, catalysts based on aluminum (such as $AlF_3$ and $Al_2O_3$ and oxyfluoride of alumina and aluminum fluoride).

Generally speaking, catalysts that can be used are chromium oxyfluoride, aluminum fluoride and oxyfluoride, and supported or unsupported catalyst containing a metal such as Cr, Ni, Zn, Ti, V, Zr, Mo, Ge, Sn, Pb, Mg. Reference can also be made to the disclosures of WO-A-2007/079431, at page 7, lines 1-5 and 28-32, EP-A-939071, at paragraph [0022], WO 2008/054781 at page 9 line 22 to page 10 line 34, WO 2008/040969 in claim 1, all incorporated herein by reference.

A preferred embodiment uses a particular catalyst, which is a supported mixed catalyst, containing both chromium and nickel. The molar ratio Cr:Ni, with respect to the metallic element is generally between 0.5 and 5, for example between 0.7 and 2, including close to 1. The catalyst may contain from 0.5 to 20% chromium and 0.5 to 20% nickel in weight, preferably between 2 and 10% of each metal.

The metal in the catalyst is converted to metal derivatives during activation (or regeneration), including oxides, halides or halide oxides.

As far as supported catalysts are concerned, the catalyst support can be selected from materials known in the art to be compatible with HF at higher temperature and pressure. For example, fluorinated alumina, prefluorinated activated carbon, graphite or fluorinated graphite are suitable catalyst supports.

The support is preferably made from aluminum. There are several possible carriers such as alumina, activated alumina or aluminum derivatives. These derivatives include aluminum halides and halide oxides of aluminum, for example described in U.S. Pat. No. 4,902,838, or obtained by the activation process.

Reference can be made to WO 2009/118628, and especially to the disclosure of the catalyst from page 4, line 30 to page 7, line 16, which is incorporated herein by reference.

According to another embodiment, the process uses a high surface area Cr based catalyst which is preferably unsupported. A preferred catalyst is a high surface area unsupported chromium oxide catalyst.

The catalyst can optionally contain a low level of one or more co-catalyst such as Co, Zn, Mn, Mg, V, Mo, Te, Nb, Sb, Ta, P and Ni salt. A preferred co-catalyst is nickel. Another preferred co-catalyst is magnesium.

The preferred unsupported chromium catalyst can optionally contain low levels of one or more co-catalysts selected from cobalt, nickel, zinc or manganese, prepared by processes known in the art, such as impregnation, mixed powder and the like.

The amount of co-catalyst, when present, can be varied between 1 to 10 wt %, preferable between 1 to 5 wt %. The co-catalyst can be added to the catalyst by processes known in the art such as adsorption from an aqueous or organic solution, followed by solvent evaporation. The preferred catalyst in this embodiment is pure chromium oxide with nickel or zinc as a co-catalyst. Alternatively the co-catalyst can be physically mixed with the catalyst via grinding to produce an intimate mixture. An alternative catalyst is a mixed chromium/nickel catalyst supported on fluorinated alumina. U.S. Pat. No. 5,731,481, incorporated herein by reference, discloses a method of preparation of this alternative catalyst.

The catalyst, before activation, is subjected to a drying step, preferably comprises passing a drying gas, preferably nitrogen. The drying step can be carried out at a pressure of from atmospheric pressure up to 20 bars. The temperature of the catalyst during drying step can range from room temperature up to 400° C., preferably from about 100° C. to about 200° C. at a contact time from about 1 to 100 s, preferably from about 10 to 40 s, for approximately 1 to 50 hours, preferably between 5 to 20 hours.

After the drying step, the catalyst needs to be activated in order to reach the best level of catalyst activity.

Activation of the Catalyst

The present inventors have found that the activation of the above catalysts using an oxidizing agent-containing gas flow makes it possible to significantly improve the efficiency of the fluorination process.

The activation process comprises activating the catalyst using one activating agent or two activating agents, in two steps or in a single step. One of the activating agents is an oxidizing agent, such as oxygen or an oxygen/nitrogen mixture or air or chlorine. The other activating agent (if present) can be HF.

According to one embodiment, the activation process is a two step-activation process, firstly with the oxidizing agent as a first activating agent, and then with HF as a second activating agent. First, the fresh catalyst is treated with the oxidizing agent. The temperature during this activation step can range from about 250 to about 500° C., preferably from about 300 to about 400° C., with a contact time of from about 1 to about 200 s, for about 10 to about 200 hours. Then, the catalyst is treated with HF. The temperature of the activation step with HF as an activating agent can range from about 100° C. to about 450° C., preferably from about 200 to about 300° C., with a contact time of from about 1 to about 100 s, for about 1 to about 50 hours.

According to another embodiment, the activation process is a two step-activation process, firstly with HF as a first activating agent, then with the oxidizing agent as a second activating agent. First the fresh catalyst is treated with HF. The temperature of the activation step with HF as an activating agent can range from about 100 to about 450° C., preferably from about 200 to about 300° C., with a contact time of from about 1 to about 100 s, for about 1 to about 50 hours. Then, the catalyst is treated with the oxidizing agent. The temperature of this activation step can range from about 250 to about 500° C., preferably from about 300 to about 400° C., with a contact time of from about 1 to about 200 s, for about 10 to about 200 hours.

According to another embodiment, the activation process is a two step-activation process comprising an activation performed by running the fluorination reaction for an initial period of time, followed by the activation with the oxidizing agent. The fluorination reaction can be carried out for about 6 to about 100 hours (for example for less than 50 hours). The HF molar ratio during the fluorination reaction can range from about 2 to about 40. The temperature of the activation step with the oxidizing agent can range from about 250 to about 500° C., preferably from about 300 to about 400° C., with a contact time of from about 1 to about 200 s, for about 10 to about 100 hours. Both steps can be repeated, until the catalyst activity reaches its best level.

According to another embodiment, the activation process is a one step-activation process with HF plus the oxidizing agent. The proportion of oxidizing agent in the mixture of HF and oxidizing agent can range from about 2 to about 98 mol %. The temperature of the activation step can range from about 200 to about 450° C., with a contact time of from about 1 to about 200 s, for about 10 to about 200 hours.

According to another embodiment, the activation process is a one step-activation process with only the oxidizing agent (without HF). The temperature of this activation step can range from about 250 to about 500° C., preferably from about 300 to about 400° C., with a contact time of from about 1 to about 200 s, for about 10 to about 300 hours.

The above activation processes can be carried out at a pressure of from atmospheric pressure up to about 20 bars.

Regarding the above activation steps with HF, HF can be fed to the system with an inert gas such as nitrogen. The proportion of HF can range from about 1 to about 100 mole % of the mixture.

Regarding the above activation steps with the oxidizing agent, the oxidizing agent can be fed to the system with an inert gas such as nitrogen. The proportion of oxygen or chlorine can then range from about 1 to 100 mole % of the mixture.

The activation with the oxidizing agent-containing gas flow should preferably be performed during at least 1 hour, preferably at least 2 hours, more preferably at least 4 hours, even more preferably at least 10 hours, most preferably at least 15 hours, at a temperature of from 250 to 500° C., preferably from 300 to 400° C., more preferably from 350 to 380° C. A temperature of approximately 370° C. is for example appropriate.

When the activation process comprises two steps (such as one with a first activating agent and the other one with a second activating agent), these steps can be repeated one, two or more times in an alternated manner.

Regeneration of the Catalyst

The present inventors have also found that the efficiency of the fluorination reaction tends to decrease over time, but that it can be increased again up to, and even above, the initial efficiency, by subjecting the catalyst to regeneration stages wherein it is contacted with an oxidizing agent-containing gas flow, in a similar way as during the initial activation stage.

According to one embodiment, each regeneration stage is a one-step regeneration stage, which is carried out with oxygen or air or an oxygen/nitrogen mixture. The temperature during the regeneration step can range from about 250 to about 500° C., with a contact time of from about 1 to about 200 s, for about 10 to about 200 hours. The regeneration step can be carried out at a pressure from atmospheric pressure to about 20 bars.

According to another embodiment, each regeneration stage is a one-step regeneration stage, which is carried out with oxygen or air or an oxygen/nitrogen mixture and HF. The temperature during the regeneration step can range from about 250 to about 500° C., with a contact time of from about 1 to about 200 s, for about 10 to about 200 hours. The regeneration step can be carried out at a pressure from atmospheric pressure to about 20 bars. The proportion of oxygen can range from about 2 to about 98 mol % relative to the mixture of oxygen plus HF, and from about 20 to about 100 mol % relative to the mixture of oxygen plus nitrogen.

When reaction stages alternate with regeneration stages, the duration of each reaction stage can be from 50 to 2000 hours, preferably from 200 to 1000 hours, and the duration of each regeneration stage can be from 10 to 200 hours, preferably from 15 to 60 hours.

EXAMPLES

The following examples illustrate the invention without limiting it.

The equipment used comprises a tubular reactor of an internal diameter of 19 mm, made of INCONEL® alloy 600 surrounded by a tubular oven. It is also equipped with pressure and temperature controllers. The reactants, preliminarily mixed owing to a static stirrer heater, are introduced in gaseous phase at the top of the reactor.

At the outlet of the reactor, a sample of the products of the reaction is taken, washed by a pre-column and analyzed online by a gas phase chromatography equipped with low polarity capillary column.

The analysis is carried out by gas phase chromatography using a column CP Sil 8CB, dimensions 50 m×0.32 mm×5 µm and a column packed, 1% SP1000/carbopack B, 60/80 mesh 5 m of length. The programming of temperature of the oven is the first one: 40° C. during 10 min then slope of 10° C./min until 250° C. and the second one: 40° C. during 20 min then slope of 10° C./min until 180° C.

Considering that xi is the initial amount of moles of raw material and xf the total final amount of moles of raw material, conversion (%) is: (xi−xf)/xi×100. Selectivity of a product is calculated by the ratio between the amount of moles recovered of this product and the total amount of moles of products being the result of the reaction of the raw material.

Some air is added in order to maintain the catalyst activity.

The contact time is defined as the ratio of the volume of catalyst bed on the total volume flow rate in the experimental conditions of temperature and pressure. The molar ratio of HF is defined as the ratio between the molar flow rate of HF and the molar flow rate of HFCO-1233xf. The molar ratio of oxygen is defined as the ratio between the molar flow rate of oxygen and the molar flow rate of HFCO-1233xf.

Example 1: Fluorination of HFCO-1233xf, Activation with an Initial Fluorination Reaction and then a Treatment with Air Fluorination of HFCO-1233xf was performed in the reactor described above with 73 cm$^3$ of Ni—Cr catalyst supported on AlF$_3$.

The catalyst used was a mixed nickel/chromium catalyst having an atomic ratio Ni/Cr of 1, supported on alumina fluoride and prepared by impregnating solutions of nickel and chromic anhydride (CrO$_3$). After impregnation and drying, the solid was treated at a temperature between 320° C. and 390° C. in the presence of a mixture of hydrofluoric acid and nitrogen (concentration by volume of 5 to 10% of this acid in nitrogen).

The activation process comprised 1) catalyst fluorination performed by running the fluorination reaction during 46 hours at temperature of 340° C., a contact time of 6 and 12 s, a molar ratio of HF of 23 and 4 mol % of oxygen per mole of HFCO 1233xf; and 2) treatment under air at 370° C. and 1.5 L/h during 64 hours.

The reactor was continuously fed with 8.1 g/h of anhydrous HF and 2.2 g/h of HFCO-1233xf at atmospheric pressure. Thus, the contact time was 12.2 s, the molar ratio of HF was 24, and the reaction temperature was 350° C. The amount of oxygen was 4 mol % with respect to the amount of HFCO-1233xf. The conversion of HFCO 1233xf was 40.8%. Complete results are provided in Table 1 below.

Example 2: Fluorination of HFCO-1233xf, Catalyst of Example 1 Reused After Regeneration With the same catalyst described in example 1, a regeneration step was performed with a treatment under air at 1.5 L/h, 370° C. during 16 h. Then, the reactor was continuously fed during 100 h with 4.4 g/h of anhydrous HF and 1.2 g/h of HFCO-1233xf at atmospheric pressure. Thus, the contact time was 22.4 s, the molar ratio of HF was 24, and the reaction temperature was 350° C. The amount of oxygen was 9 mol % with respect to the amount of HFCO-1233xf. The conversion was 64.4%, but a deactivation of the catalyst was observed over time and conversion finally reached 33.4%. Complete results are provided in Table 1 below.

Example 3: Fluorination of HFCO-1233xf, Activation with an Initial Fluorination Reaction and then a Treatment with Air Fluorination of HFCO-1233xf was performed in the reactor described above with 73 cm$^3$ of Ni—Cr catalyst supported on AlF$_3$ described in example 1.

The activation process comprised five cycles of: 1) catalyst fluorination performed by running the fluorination reaction during 6 and 30 hours in the conditions set forth below, followed by 2) a treatment of the catalyst with air at 370° C. and 1.5 L/h during 16 and 64 hours.

For the purpose of the fluorination reaction, the reactor was continuously fed during 32 h with 3.4 g/h of anhydrous HF and 1 g/h of HFCO-1233xf at atmospheric pressure. Thus, the contact time was 29 s, the molar ratio of HF was 22, and the reaction temperature was 350° C. The amount of oxygen was 7 to 8 mol % with respect to the amount of HFCO-1233xf. The conversion was 69.7% and decreased over time until 54.7%. Then, a regeneration step under 1.5 L/h of air at 370° C. during 16 h was performed. After this step, an even higher conversion rate than the one initially observed (72.4%) was recovered.

Complete results are provided in Table 1 below.

Example 4 (Comparative Example): Fluorination of HFCO-1233xf, Activation with HF Only Fluorination of HFCO-1233xf was performed in the reactor described above with 73 cm$^3$ of Ni—Cr catalyst supported on AlF$_3$ described in example 1.

After an activation of the catalyst with HF at atmospheric pressure and 350° C., without treatment under air, the reactor was continuously fed with 7.6 g/h of anhydrous HF and 2.2 g/h of HFCO-1233xf at atmospheric pressure. Thus, the contact time was 12.7 s, the molar ratio of HF was 23, and the reaction temperature was 350° C. The amount of oxygen was 4 mol % with respect to the amount of HFCO-1233xf. The conversion of HFCO 1233xf was 9.1%.

TABLE 1

| | results | | | | | | | | |
|---|---|---|---|---|---|---|---|---|---|
| | Ex.1 | Ex.2 | | | | Ex.3 | | | Ex.4 |
| Catalyst volume (cm$^3$) | 73 | 73 | 73 | 73 | 73 | Catalyst regeneration | 73 | 73 | |
| Molar ratio of HF | 24 | 24 | 24 | 22 | 22 | | 22 | 23 | |
| Contact time (s) | 12.2 | 22.4 | 22.4 | 29 | 29 | | 29 | 12.7 | |

TABLE 1-continued results

| | Ex.1 | Ex.2 | | Ex.3 | | | Ex.4 | |
|---|---|---|---|---|---|---|---|---|
| Molar ratio O$_2$/HFCO-1233xf | 0.04 | 0.09 | 0.09 | 0.08 | 0.08 | | 0.08 | 0.04 |
| Catalyst run time with HFCO-1233xf (h) | 5.9 | 5.7 | 101 | 7 | 33 | | 34.5 | 1 |
| Conversion (GC % area) | 40.8 | 64.4 | 33.4 | 69.7 | 54.7 | | 72.4 | 9.1 |
| Selectivity in HFO-1234yf | 66.4 | 63.9 | 63.8 | 65.7 | 64.6 | | 65.1 | 63.7 |
| Selectivity in HFC-245cb | 31.4 | 31.9 | 31.9 | 32.8 | 32.3 | | 32.6 | 31.8 |

Example 5 (Comparative Example): Fluorination of HFCO-1233xf without Specific Activation Fluorination of HFO-1233xf was performed in the reactor described above with 73 cm$^3$ of Ni—Cr catalyst supported on AlF$_3$ described in example 1.

After loading of the catalyst in the reactor, the catalyst was dried with nitrogen at 220° C. during 16 hours. Then the reactor temperature was brought to 350° C. and the reactor was continuously fed with 4.5 g/h of anhydrous HF and 1.2 g/h of HFCO-1233xf and air at atmospheric pressure and 350° C. The contact time was 22 s, and the HF MR was 24. The amount of oxygen was 9 mol % with respect to the amount of HFCO-1233xf. The conversion of HFCO 1233xf reached 14.8% after 24 hours of reaction.

Complete results are provided in Table 2 below.

Example 6: Fluorination of HFCO-1233xf, Activation with Air Only

Fluorination of HFCO-1233xf was performed in the reactor described above, with 73 cm$^3$ of Ni—Cr catalyst supported on AlF$_3$ described in example 1.

First, the catalyst was dried with nitrogen at 220° C. during 16 hours. Then, nitrogen feeding was stopped and air was introduced in the reactor during 2 hours. After that, the oven temperature was brought to 370° C. and maintained at this temperature during 64 hours. After this activation of the catalyst, the oven temperature and air flow rate were adjusted for the following experiment. The reactor was continuously fed with 5.0 g/h of anhydrous HF and 1.1 g/h of HFCO-1233xf at atmospheric pressure. The contact time was 20 s, the HF MR was 30, and the reaction temperature was 350° C. The amount of oxygen was 9 mol % with respect to the amount of HFCO-1233xf. The conversion of HFCO 1233xf reached 18.5% after 22 hours of reaction.

Complete results are provided in Table 2 below.

Example 7: Fluorination of HFCO-1233xf, Activation with HF and then Air

Fluorination of HFCO-1233xf was performed in the reactor described above, with 73 cm$^3$ of Ni—Cr catalyst supported on AlF$_3$ described in example 1.

First, the catalyst was dried at atmospheric pressure with nitrogen at 220° C. during 16 hours. Then, HF was introduced and maintained during 2 hours. The oven temperature was brought to 350° C. and maintained with HF during 3 hours. Next, HF was replaced by air at 1.5 L/hr and the oven temperature was brought to 370° C. and maintained during 16 hours. After that, the oven temperature and the air flow rate were adjusted for the following experiment and HF and HFCO-1233xf were introduced in the reactor. The reactor was continuously fed with 4.1 g/hr of anhydrous HF and 1.0 g/hr of HFCO-1233xf) at atmospheric pressure. The contact time was 24 s, the HF MR was 26, and the reaction temperature was 350° C. The amount of oxygen was 8 mol % with respect to the amount of HFCO-1233xf. The conversion of HFCO-1233xf reached 58.6% after 10 hours of reaction.

Complete results are provided in Table 2 below.

TABLE 2 results

| | Ex. 5 | Ex. 6 | Ex. 7 |
|---|---|---|---|
| Catalyst volume (cm$^3$) | 73 | 73 | 73 |
| Molar ratio of HF | 24 | 30 | 26 |
| Contact time (s) | 22 | 20 | 24 |
| Molar ratio O$_2$/HFCO-1233xf | 0.09 | 0.09 | 0.08 |
| Catalyst run time with HFCO-1233xf (h) | 24 | 22 | 10 |
| Conversion (GC % area) | 14.8 | 18.5 | 58.6 |
| Selectivity in HFO-1234yf + HFC-245cb | 98.6 | 97.3 | 97.3 |

The invention claimed is:

1. A fluorination process, comprising:
an activation stage comprising the following steps, in succession:
   i. reacting a chlorinated compound selected from the group consisting of hydrochlorocarbons, hydrochlorofluorocarbons and hydrochlorofluoroolefins with hydrogen fluoride in gas phase in the presence of a chromium-based fluorination catalyst, and
   ii. contacting the chromium-based fluorination catalyst with a first oxidizing agent-containing gas flow comprising an oxidizing agent and hydrogen fluoride, wherein the proportion of oxidizing agent in the first oxidizing agent-containing gas flow is from 2 to 98 mol %, relative to the total amount oxidizing agent and hydrogen fluoride;
at least one reaction stage comprising reacting the chlorinated compound with hydrogen fluoride in gas phase in the presence of the fluorination catalyst, so as to produce a fluorinated compound; and
at least one regeneration stage comprising contacting the fluorination catalyst with a second oxidizing agent-containing gas flow.

2. The process of claim 1, wherein the first and/or second oxidizing agent-containing gas flows comprise an oxygen-containing gas flow.

3. The process of claim 1, wherein the activation stage and/or the at least one regeneration stage comprise contacting the fluorination catalyst with the first and/or second oxidizing agent-containing gas flows for at least 2 hours.

4. The process of claim 1, wherein the second oxidizing agent-containing gas flow contains hydrogen fluoride in addition to the oxidizing agent, and wherein the proportion of oxidizing agent in the second oxidizing agent-containing gas flow is from 2 to 98 mol %, relative to the total amount oxidizing agent and hydrogen fluoride.

5. The process of claim 1, wherein the second oxidizing agent-containing gas flow does not contain hydrogen fluoride.

6. The process of claim 1, wherein the first and/or second oxidizing agent-containing gas flow comprise air.

7. The process of claim 1, wherein the activation stage and/or the at least one regeneration stage comprise contacting the fluorination catalyst with a hydrogen fluoride gas flow, either:
- before contacting the fluorination catalyst with the oxidizing agent-containing gas flow; or
- after contacting the fluorination catalyst with the oxidizing agent-containing gas flow.

8. The process of claim 1, wherein the first and/or second oxidizing agent-containing gas flow is/are contacted with the fluorination catalyst at a temperature of from 250 to 500° C.

9. The process of claim 1, wherein the fluorinated compound is a fluoroolefin.

10. The process of claim 1, wherein the fluorination catalyst is a supported catalyst.

11. The process of claim 1, wherein the fluorination catalyst is an unsupported catalyst.

12. The process of claim 1, wherein the fluorination catalyst further comprises a co-catalyst selected from the group consisting of Co, Zn, Mn, Mg, V, Mo, Te, Nb, Sb, Ta, P, Ni and mixtures thereof.

13. The process of claim 12, wherein the co-catalyst is present in an amount from about 1-10 wt % of said fluorination catalyst.

14. The process of claim 1, wherein the fluorination catalyst is a mixed chromium/nickel catalyst.

15. The process of claim 1, wherein the chlorinated compound is 2-chloro-3,3,3-trifluoro-1-propene.

16. The process of claim 1, wherein the at least one reaction stage is carried out at a pressure of from 1 to 20 bars.

17. The process of claim 1, wherein the at least one reaction stage is carried out at a temperature of from 200 to 450° C.

18. The process of claim 1, wherein the contact time between hydrogen fluoride and the chlorinated compound during the at least one reaction stage is from 6 to 100 s.

19. The process of claim 1, wherein the at least one reaction stage is carried out in the presence of an oxidizing agent.

* * * * *